[19] United States Patent
Gazdar et al.

[11] Patent Number: 4,892,829
[45] Date of Patent: Jan. 9, 1990

[54] HUMAN PLASMA CELL LINE HAVING REARRANGED C-MYC PROTO-ONCOGENE

[75] Inventors: Adi F. Gazdar, Potomac; Herbert K. Oie, Rockville, both of Md.

[73] Assignee: The United States of America as represented by the Secretary of the Department of Health and Human Services, Washington, D.C.

[21] Appl. No.: 854,493

[22] Filed: Apr. 22, 1986

[51] Int. Cl.[4] .................. C12N 5/00; C12N 15/00; C12R 1/91
[52] U.S. Cl. ................. 435/240.2; 435/948; 435/240.25
[58] Field of Search ............... 435/240.2, 948, 240.25

[56] References Cited

U.S. PATENT DOCUMENTS 4,434,230  2/1984  Ritts, Jr. ........................ 435/948
4,542,096  9/1985  Leder .............................. 436/504

OTHER PUBLICATIONS

Benjamin et al, Proc. Natl. Acad. Sci. 81, pp. 3547–3551 (1984).
Adams et al, Proc. Natl. Acad. Sci. 80, pp. 1982–1986 (1983).
Bernard et al, E.M.B.O. Journal 2(12), pp. 2375–2383 (1983).
Nilsson, et al. *Clin Exp. Immunol.*, (1970) 7, 477–489, Established Immunologlobulin Producing Myeloma (IgE) and Lymphoblastoid (IgG) Cell Lined from an IgE Myeloma Patient.
Karpas, et al. *Science*, vol. 216, May 28, 1982, 997–999, Human Myeloma Cell Line Carrying a Philadelphia Chromosome.
Matsuoka, et al., *P.S.E.B.M.*, 1967, V. 125, May 8, 1967, 1246–1250, Production of Free Light Chains of Immunoglobulin by a Hemapoietic Cell Line Derived from a Patient with Multiple Myeloma.

*Primary Examiner*—John Edward Tarcza
*Attorney, Agent, or Firm*—Fleit, Jacobson, Cohn, Price, Holman & Stern

[57] ABSTRACT

Using a serum-free defined medium, a human cell line, NCI-H929, was established from a malignant effusion occuring in a patient with IgAk myeloma. The cultured cells have the morphologic, ultrastructural, biochemical, immunologic and cytochemical features of plasma cells. The cells have rearranged alpha and kappa genes and synthesize and secrete very high amounts of IgAk ($>80$ $\mu g/10^6$ cells/24 hr). The cells express surface immunoglobulin (alpha and kappa), the plasma cell antigen PCA-1, the transferrin receptor (T9) and T10, but lack antigens associated with earlier stages of B cell development (HLA-DR, B1, B2, B4, CALLA), as well as other leukocyte-macrophage antigens and Epstein-Barr virus nuclear antigen. While the tumor cells were predominantly near-diploid, the cultured cells are predominantly near-tetraploid with six copies of chromosome 8, four to six of which have an 8q+ abnormality. The cultured cells have a rearrangement of the cellular c-myc proto-oncogene (located at 8q24) and express c-myc RNA.

5 Claims, 6 Drawing Sheets

FIG. 1A
FIG. 1B
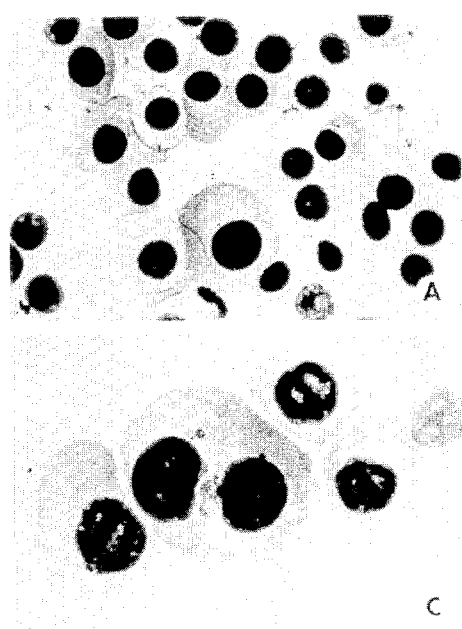
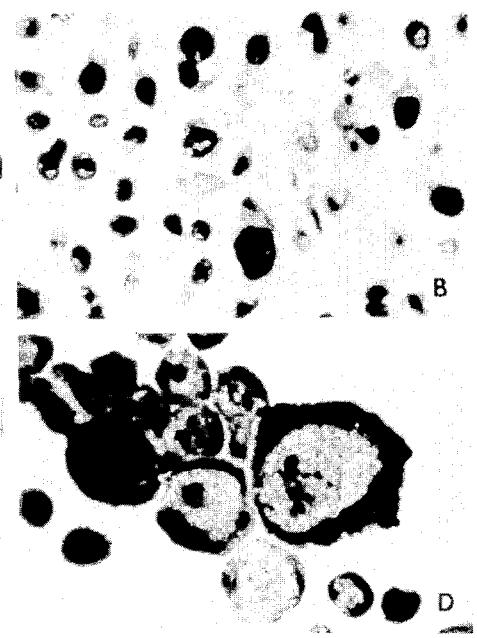
FIG. 1C
FIG. 1D

HUMAN PLASMA CELL LINE HAVING REARRANGED C-MYC PROTO-ONCOGENE

BACKGROUND OF THE INVENTION

1. Technical Field

The present invention is related to the establishment and characterization of a new, cultured, human plasma cell myeloma line. More particularly, the present invention is related to a unique human plasma cell line, designated NCI-H929, having rearranged in its genome the alpha and kappa genes and which is capable of synthesizing and secreting high amounts of IgAk ($>80$ $\mu/10^6$ cells/24 hr), said cell line also having a rearranged cellular c-myc proto-oncogene.

2. State of the Art

Despite intense efforts in many laboratories during the past twenty years, plasma cell (PC) myelomas and leukemias have been one of the most difficult of human malignancies to establish in continuous culture (Karpas et al., Science 216:997, 1982). While a modest number of Holman & Stern, Chartered Folio P49604 'plasmacytoid' cell lines have been reported, the vast majority of these are lymphoblastoid cell lines (LCLs), which result from in vitro transformation of non-malignant B cells by Epstein-Barr virus (Nilsson et al., Advan. Cancer Res. 37:319, 1982). In contrast, many mouse plasmacytoma and human Burkitt lymphoma (BL) lines exist (Marcu et al., Proc. Natl. Acad. Sci. USA 80:523, 1983; Taub et al., Cell 36:339, 1984). In both of these otherwise very different B cell tumors, specific reciprocal translocations occur which bring the cellular myc proto-oncogene (c-myc gene) and an immunoglobulin (Ig) gene segment into the same chromosomal region. These events result in the preferential transcription, and perhaps, abnormal regulation of the translocated c-myc gene. While similar molecular events probably occur in rat PC tumors (Sumegi et al., Nature 306:497, 1983), human myelomas have not been associated with rearrangement or inappropriate transcription of c-myc, nor with structural abnormalities of its chromosomal location (8q24) (Philip, Cytogenet 2:79, 1980).

SUMMARY OF THE INVENTION

It is, therefore, an object of the present invention to establish in continuous culture a new cell line derived from malignant human plasma cells, said cell line being designated herein as NCI-H929.

It is a further object of the present invention to have a rearranged c-myc oncogene in said new plasma cell line.

Other objects and advantages will become evident upon a reading of the following detailed description of the present invention.

BRIEF DESCRIPTION OF DRAWINGS

These and other objects, features and many of the attendant advantages of the invention will be better understood upon a reading of the following detailed description when considered in connection with the accompanying drawings wherein:

FIG. 1 shows morphological appearances of NCI-H929 tumor and cultured cells. FIG. 1a, bone marrow aspirate at diagnosis. Almost all the cells are nucleated PCs, with occasional giant forms. Wright-Giemsa. FIG. 1b, histological section of right pleura at autopsy. The cellular infiltrate consists predominantly of abnormal PCs with many hyperchromatic and bizarre forms. Hematoxylin and eosin. FIG. 1c, appearance of cultured cells. The very large cells are plasmacytoid, with prominent nucleoli, occasional giant or multinucleated forms, and perinuclear clear areas (hof). Wright-Giemsa. FIG. 1d, immunocytochemical demonstration of kappa light chain. The staining is predominantly cytoplasmic with sparing of the hof areas. Immunoperoxidase technique. All magnifications $\times 300$;

Figure 6:
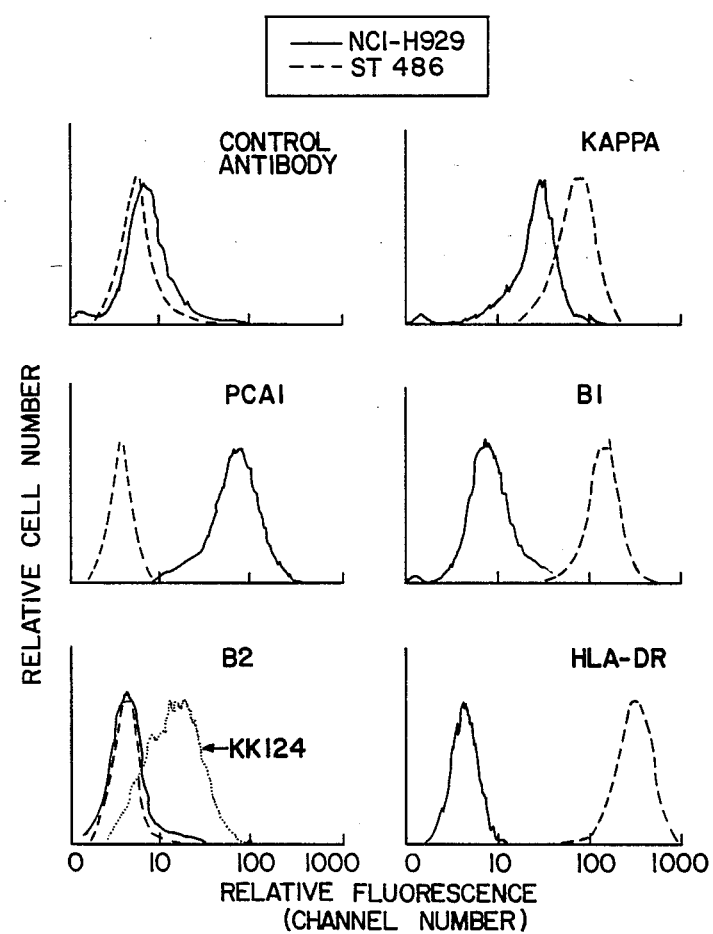
Figure 7:
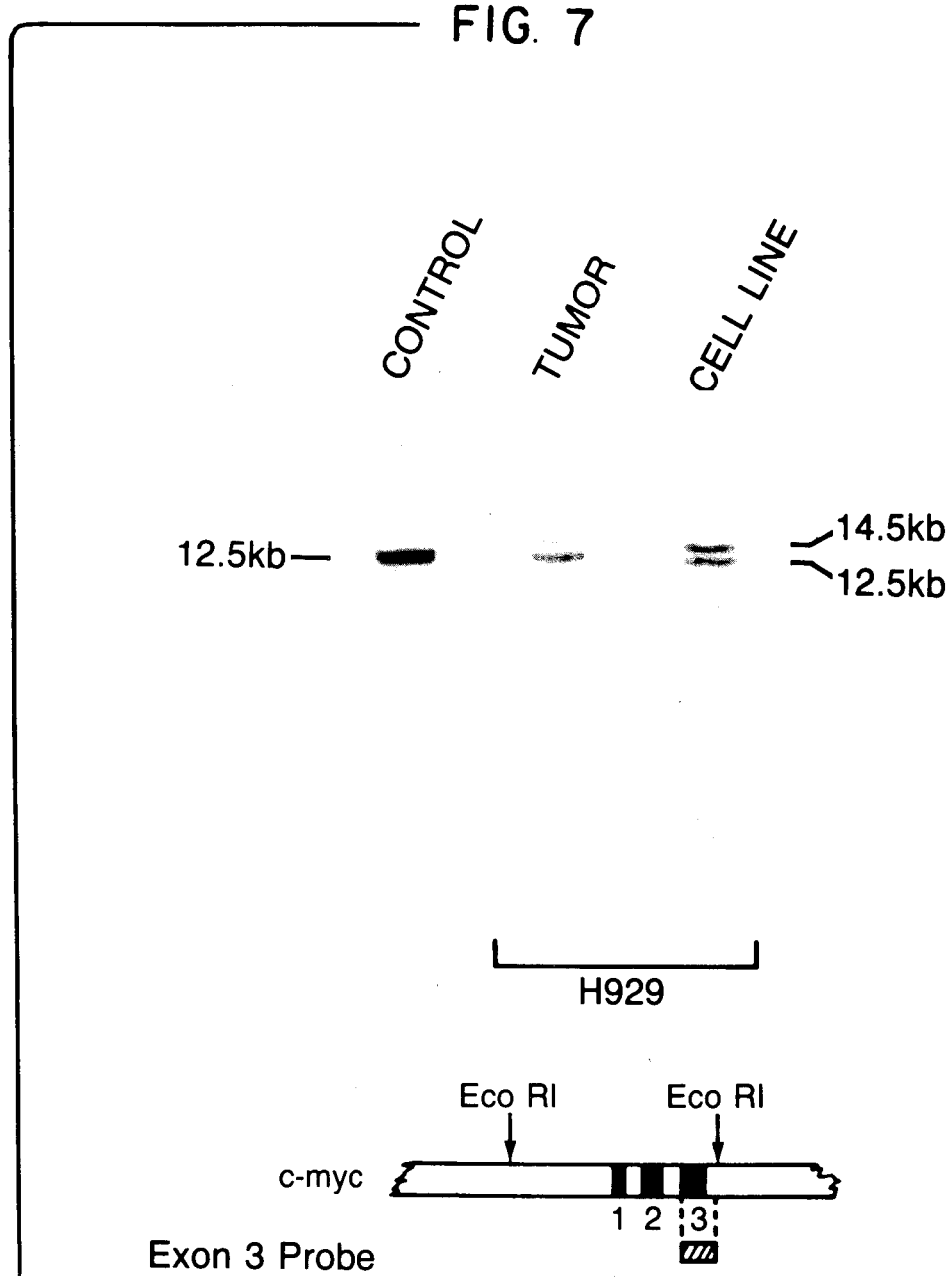

Three DNA samples (lanes 1–3), a control T-cell line, NCI-H929 tumor and cell line, are shown in a BAM HI Southern genomic blot analysis probed with human alpha constant region-one. In all three DNAs the germline 14.5 kb band and in NCI-H929 Tumor and cell line a rearranged 13.0 kb band is identified (the 13.0 kb band is faint in NCI-H929 tumor). In lanes 4–6 analysis using the same probe is shown on three RNA samples, control (KK124, a mu and kappa producing Burkitt lymphoma cell line) and NCI-H929 tumor and cell line synthesize a 1.9 kb Ig alpha mRNA. In lanes 7–9 three DNA samples, a control T-cell line and NCI-H929 tumor and cell line were digested with BAM HI restriction endonuclease and probed with human kappa constant region. All three DNAs contain the germline 12.0 kb band and in NCI-H929 tumor and cell line a 14.5 kb rearranged band is identified. Lanes 10–12 present a Northern blot analysis using a kappa constant probe which identifies a 1.2 kb mRNA in control (KK124) and NCI-H929 tumor and cell line RNA;

FIG. 6 demonstrates expression of surface antigens on PC line NCI-H929 and BL line St 486. NCI-H929 lacks expression of B1, B2 and HLA-DR; has weak expression of kappa light chain and strong expression of PCA-1. ST 486 lacks expression of B2 and PCA-1; has moderate expression of kappa light chain and very strong expression of HLA-DR. Because ST 486, an EBNA negative BL line, lacks expression of B2, an epitope of the common CR2 and EBV receptor, B2 expression by KK124, an EBNA positive BL line, is demonstrated; and FIG. 7 shows genomic blot analysis for c-myc in NCI-H929 tumor and cell line. Three DNA samples, control, NCI-H929 tumor and cell line are shown in an Eco RI Southern genomic blot analysis. The third exon of human c-myc probe identifies the germline 12 kb Eco RI fragment in all three samples and an additional rearranged 14.5 kb band is present in the tumor and cell line. The relative intensity of the rearranged band is greater in the cell line than in the tumor sample.

DETAILED DESCRIPTION OF INVENTION

The above and many other objects and advantages of the present invention are achieved by a human plasma cell myeloma line in continuous in vitro culture, said cell line having a rearranged c-myc proto-oncogene. Of course, the cell line can be cryopreserved for convenient storage.

It is noted that all scientific and/or technical terms employed herein have the same meaning as generally understood by one of ordinary skill in the art to which the invention belongs. All publications cited hereunder are incorporated herein by reference. Although any similar or equivalent methods and materials may be employed in the practice, testing and the like of the present invention, the preferred methods and materials are now described.

The term "rearranged" as used herein means a pattern of restriction endonuclease sites that deviate from the normal human germ line DNA.

Normal and malignant PCs represent the final, terminally differentiated, highly secretory stage of B cell differentiation. They have several characteristic features including typical morphology, ultrastructure, cytochemistry, the presence of functional, rearranged, heavy and light chain genes, secretion of monoclonal Ig, a low proliferative cell fraction, loss of most B cell antigens and expression of the PC associated antigen PCA-1 (Wall et al., Ann. Rev. Immunol. 1:393, 1983; Anderson et al., Blood 63:1424, 1984; Ruiz-Arguelles et al., Blood 64:352, 1984).

Described herein is the establishment of a cell line, NCI-H929, from a malignant effusion occurring in a patient with IgAk myeloma. The patient's tumor and cultured cells have the morphologic and antigenic properties of fully differentiated malignant PCs, lack EBV nuclear antigen (EBNA), and secrete very high concentrations of IgAk ($>80\mu g/10^6$ cells/24 hr). Of major significance is the finding that a rearrangement of the c-myc oncogene is present in both the tumor and cultured cells, in association with an addition to the long arm of chromosome 8 (8q+).

MATERIALS AND METHODS

A 62 year old white woman was diagnosed as having IgAk PC myeloma. Her bone marrow was virtually replaced with immature PCs (FIG. 1a), and she had a serum IgA level of 9 g/dl. She was treated with vincristine, melphalan, cytoxan and prednisone, and achieved a brief clinical response. At relapse, nine months after diagnosis, a right pleural effusion was processed for diagnostic workup. The patient died a month later and autopsy revealed widespread infiltration of the viscera, including lungs and pleura, with malignant PCs, many of which had bizarre or multinucleated forms (FIG. 1b).

Cell culture and characterization.

The NCI-H929 cell line was initiated from the malignant pleural effusion from the patient with IgAk myeloma. The cells at the interface of a discontinuous Ficoll-Hypaque gradient were harvested, washed, resuspended in various media in 75 cm$^2$ flasks at density of about $1\times 10^6$/ml and incubated in a humidified 6% $CO_2$ atmosphere at 37° C. Cytological examination of the interface cells indicated that over 90% consisted of malignant PCs. The media used included RPMI-1640 supplemented with 10% fetal bovine serum or 10–20% patient's pleural fluid, or serum-free media capable of supporting continuous growth of the NCI-H929 cell line. An example of such a medium is an ACL-3 medium comprising RPMI-1640 medium supplemented with insulin (20 μg/ml), transferrin (10 μg/ml), sodium selenite ($2.5\times 10^{-8}$M), hydrocortisone ($5\times 10^{-8}$M), epidermal growth factor (1 ng/ml), ethanolamine/phosphorylethanolamine ($1\times 10^{-5}$M of each), triiodothyronine ($1\times 10^{-10}$M), bovine albumin (0.2%), sodium pyruvate (0.5 mM), HEPES buffer (10 mM) and extra glutamine (2 mM). Mycoplasma contamintion was tested by routine liquid and agar plate culture techniques well known in the art and by the Hoechst stain method by Microbiological Associates, Bethesda, MD. Species identification was by isoenzyme analysis using agarose electrophoresis (Authentikit apparatus and reagents, Corning Medical, Medfield, MA.).

Morphologic studies.

Air dried cytospins of cultured cells were stained with Wright-Giemsa or other suitable stains. For transmission electron microscopy, cell pellets were fixed in 2.5% glutaraldehyde, post-fixed in chrome-osmium and stained with uranyl acetate following routine procedure. Thin sections were examined in a Siemens Elmiskop 1A electron microscope.

DNA index and cytogenetic studies.

The DNA index (DI) of tumor ad cultured cells was determined by flow cytometry using an EPICS V fluorescence-activated cell sorter (Coulter Electronics, Hialeah, FL.) after propidium iodide staining (Krishan, J. Cell. Biol. 66:188–193, 1975). For chromosome analysis, cells were treated with colchicine, lysed with hypotonic solution and stained with trypsin-Giemsa.

Immunoglobulin and antigen assays.

Cell lysates and clarified culture supernatant fluids were tested for the presence of Ig by double immunodiffusion assays using polyclonal antibodies to human heavy and light chains. Cytoplasmic Ig was tested by a standard immunoperoxidase method. Ig concentrations in cell lysates and fluids were quantitated by rate nephelometry with a Beckman immunocytochemistry Analyzer II (Joliff et al., Clin. Chem. 28:126, 1982). The presence of nuclear terminal deoxynucleotidyl transferase was determined by a standard immunoperoxidase method. EBNA was tested as described by Magrath et al., J. Natl. Cancer Inst. 64:465, 1980. Surface antigens were tested by incubating cells with saturating concentrations of fluorescein labelled or unlabelled monoclonal antibodies ($10^6$ cells in 100 μl at 4° C. for 30 min), washed twice and, if the primary antibody was unlabelled, incubated with fluoresceinated goat anti-mouse Ig of the appropriate class, washed twice, and analyzed for log fluorescence intensity using an EPICS V cell sorter.

Other cell lines.

The antigenic properties of NCI-H929 cells were compared with those of other B cell lineage cultures: Lymphoblastoid cell lines (LCL) (BL-2, GM 1500, CB23, LAZ409, UC729-HF$_2$ and L1 CR-LON-LMy2) and BL cell lines (ST-486, KK124, Raji, Daudi, Ramos and CW678). 'Plasmacytoid' cell lines U266, RPMI 8226, HS Sultan and ARH-77 were obtained from the American Type Culture Collection, Rockville, MD.

DNA and RNA extraction and analysis.

DNA from the NCI-H929 cell line, was prepared as described by Maniatis et al., In Molecular Cloning. A Laboratory Manual, pp. 196, (1982), directly from the cells of the pleural effusion after harvesting them from a discontinuous Ficoll-Hypaque gradient, and from a control cell line of T cell origin. The genomic DNAs were digested with Eco RI, fractionated on a 0.8% agarose gel (10μg per lane) and transferred to nitrocellulose paper according to the method of Southern, J. Molecular Biol. 98:503 (1975). RNA extracts and blots were performed as described by Chirgwin et al., Biochem. 18:5294 (1979). DNA and RNA blots were hybridized to $^{32}$P-labelled human DNA probes corresponding to: (a) Ig mu probe, a 1.3 kilobase (kb) genomic Eco RI - Eco RI fragment containing exons for the first two coding domains of the mu constant region (Ravetch et al., Proc. Natl. Acad. Sci. USA 77:6735, 1980); (b) Ig alpha probe, a genomic 4.2 kb Xho I - EcoRI fragment containing the alpha constant region (the latter side being donated by the plasmid pBR322); (c) Ig kappa probe, a 2.5 kb genomic Eco RI - Eco RI fragment containing the constant region (Hieter, et al., Cell 22:197, 1980); and (d) c-myc probe, a 1.7 kb Cla I - Eco RI fragment containing exon 3 (Battey et al., Cell 34:779, 1983). The transfers were washed at 55° C. in 15 mM NaCl/1.5 mM sodium citrate, pH 7.0, containing 0.1% NaDodSO$_4$ and visualized by autoradiography.

Establishment of cell culture.

It was found that no significant growth occurred in media supplemented with bovine serum or clarified effusion fluid. In contrast, immediate and continuous growth of cell line NCI-H929 occurred in fully defined ACL-3 medium, supra. The cultured cells have a population doubling time of about 50 hr, and grow as irregularly shaped floating cells, either singly or in small, loose clusters. Giant forms are frequent, some of which are multinucleated. Cell size varies from 20 to over 50 μ. The cell line is free of mycoplasma contamintion.

A deposit of the cultured NCI-H929 has been made at the American Type Culture Collection, Rockville, MD. under the accession number CRL 9068. Upon issuance of a patent, the deposit will continue to be viably maintained for at least 30 years and will be available to the public without restriction, of course, in accordance with the provisions of the law.

Morphologic Studies.

Figures 2A, 2B:
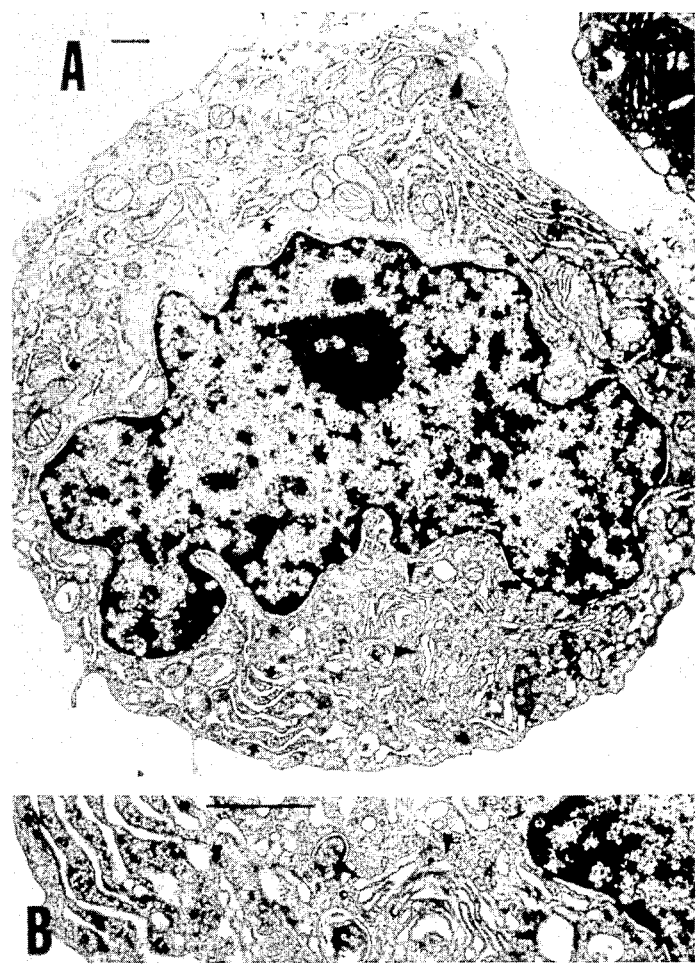
FIG. 2a and b show ultrastructure of NCI-H929 cell line. The appearance is that of an immature PC with large nucleus having a prominent nucleolus and clumped chromatin. The rough endoplasmic reticulum is extensive and arranged as perinuclear lamellae (arrows). The golgi is well developed (arrowheads). Insert (FIG. 2b) is a higher magnification of the cytoplasmic features. Bars represent one $\mu$m.

Wright-Giemsa stained cultured cells (FIG. 1c) resemble the abnormal plasma cells present at autopsy. Ultrastructural examination (FIG. 2a and b) confirmed that the cells are immature PCs, with abundant rough endoplasmic reticulum arranged in perinuclear concentric lamellae, and a prominent golgi present as multiple paranuclear apparati. Many mitochondria are present, free ribosomes are sparse, nucleoli are prominent, and the chromatin clumped. Cytochemical tests indicated that the tumor and cultured cells stain brightly with methyl green pyronin, acid phosphatase, alpha naphthyl acetate esterase and beta glucuronidase, but not with PAS.

DNA index and cytogenetic studies.

Figure 3:
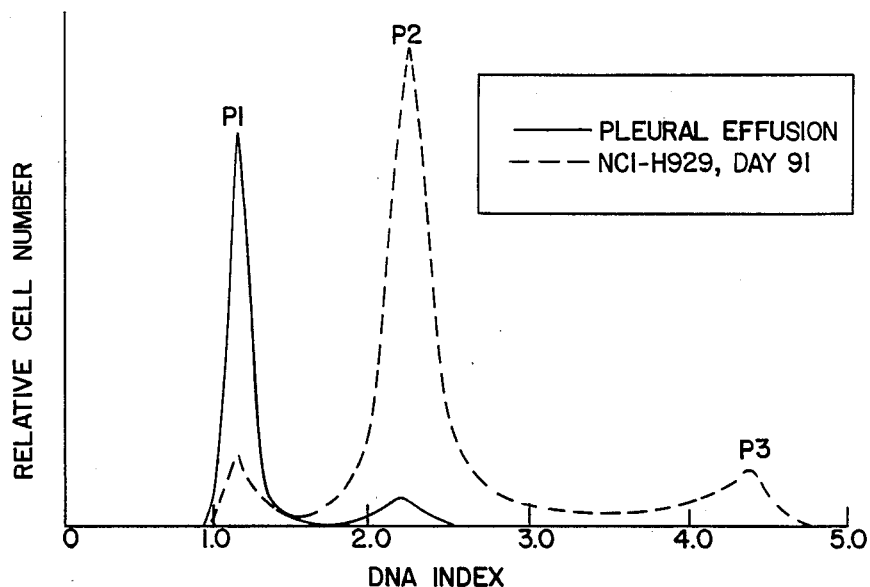
FIG. 3 shows DNA histograms of NCI-H929 malignant effusion and 91 day old culture. In both specimens all, or nearly all, of the cells are aneuploid. Of the tumor cells, 90% had a DNA index (DI) of 1.15 (peak 1), and 10% a DI of 2.3 (peak 2). In the cell culture, peak 2 is the major component (77%) and peak 1 relatively small (8%). In addition, a third peak (peak 3) is present (15%), presumably representing the dividing ($G_2$ and M) cells of peak 2.
Figure 4:
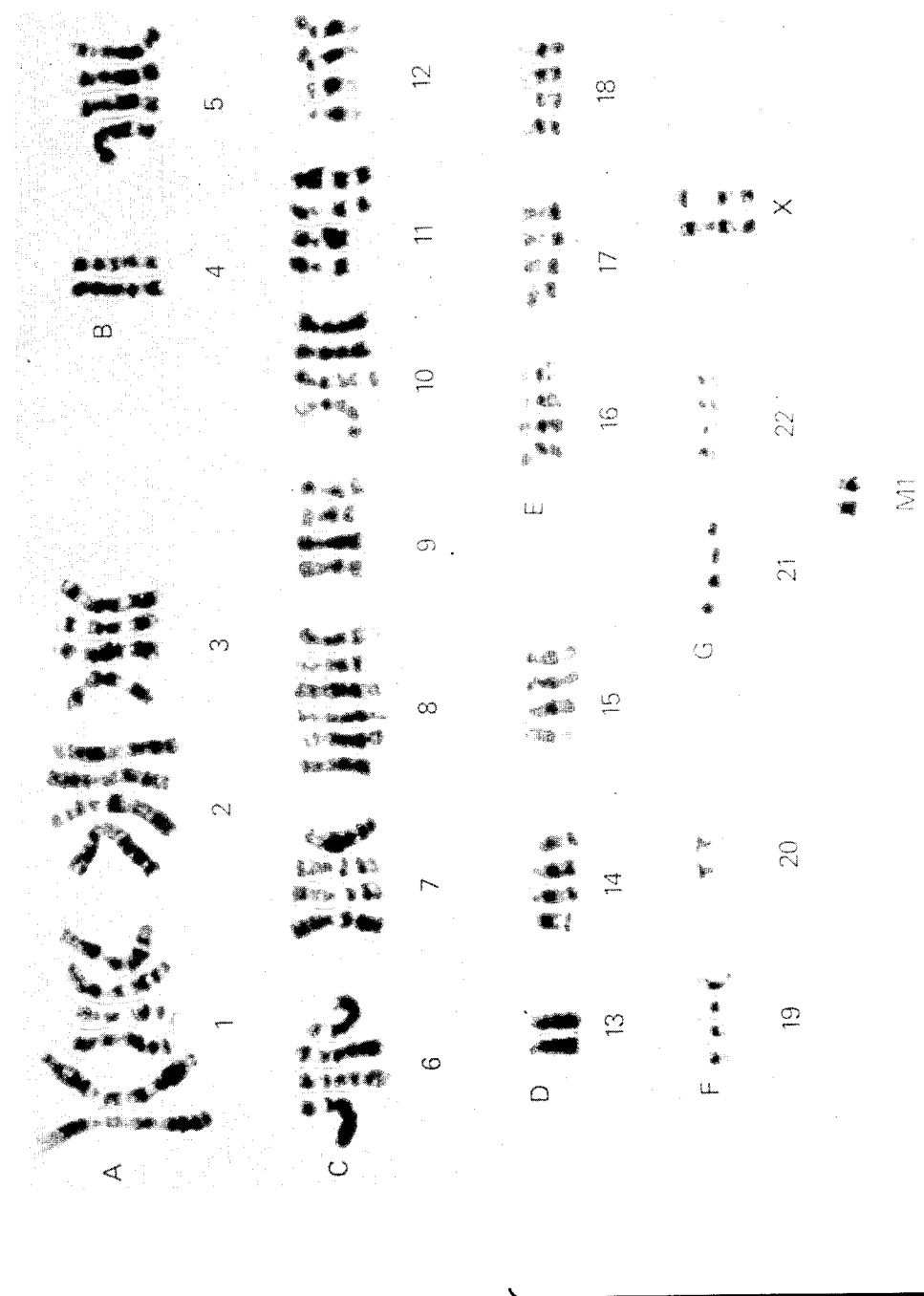
FIG. 4 shows representative G-banded karyotype of NCI-H929 cells, 87 days after initiating culture. All six copies of chromosome #1 are abnormal; the two illustrated on the left have an apparent duplication of the long arm, while the other four copies have deletions of the short arm of varying size. Of the six copies of chromosome #8, the one on the left is normal appearing; four and perhaps all five of the other copies have an 8q+ abnormality. Other consistent abnormalities included t(10q, 12p) in two of four copies, del (12p) in the other two copies of chromosome 12, and a marker chromosome (M1), possibly i(16q)

DNA histograms (FIG. 3) of the gradient concentrated pleural fluid cells indicated that almost all the cells were aneuploid, with 90% having a DNA index (DI) of 1.15 (peak 1), and 10% a DI of 2.3 (peak 2). After culture, peak 2 became the dominant population (FIG. 3). Cytogenetic tests of the cell line at day 87 of culture (FIG. 4), indicated that approximately 80% of the metaphases consisted of near tetraploid cells (90–92 chromosomes) with a minor near diploid subpopulation (44–48 chromosomes). Banding studies demonstrated a human karyotype with multiple structural abnormalities (FIG. 4). Of particular significance was the finding that six copies of two chromosomes (numbers 1 and 8) were present in the near tetraploid cells. Additional chromosomal material of unidentified origin was attached to the long arm of chromosome 8 (8q+), in at least four and usually in all six copies. All six copies of chromosome 1 were abnormal; one pair demonstrating an apparent duplication of the long arm, dup(1) (q11-25); the other 4 having a delection of the short arm of variable length.

Ig and antigen studies.

Figure 5:
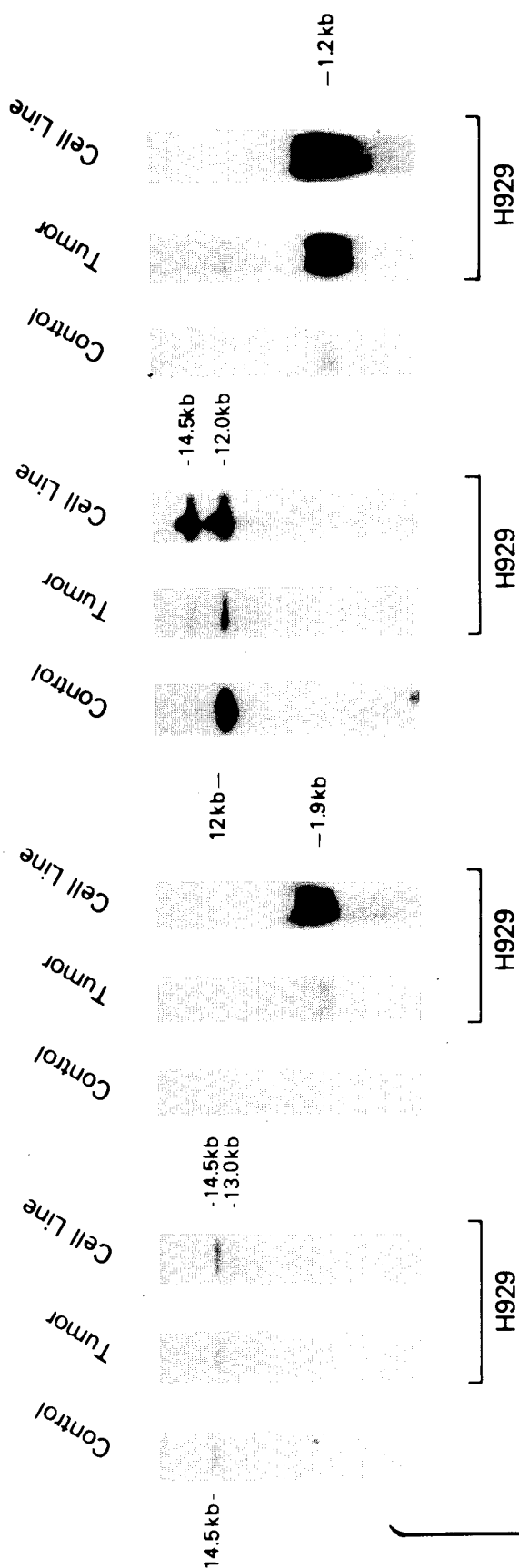
FIG. 5 shows Ig gene expression and rearrangement of NCI-H929 tumor and cell line. The figure consists of 12 lanes, which are numerically referred to in the legend sequentially from left to right.
Figure 5:
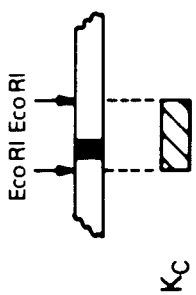
Figure 5:
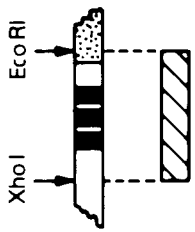

Immunodiffusion studies demonstrated that the pleural fluid, culture medium and extracts of cultured cells contained IgAk. The presence of intracytoplasmic Ig was confirmed by immunoperoxidase stain (FIG. 1d). Quantitative studies demonstrated that the cultured cells were secreting about 83 μg/10$^6$ cells/24 hr and contained 7.1 μg/10$^6$ cells of intracytoplasmic IgA. These high concentrations were confirmed by an ELISA method. DNA and RNA from the tumor and cell lines were analyzed with $^{32}$P-labelled probes derived from the Ig constant regions (FIG. 5). Patterns from both samples were the same: one germline and one identically rearranged alpha and kappa genes were noted, while both mu genes were deleted. Abundant alpha and kappa mRNA were present, confirming the IG production data (FIG. 5).

Flow cytometric studes of both tumor and cultured cells demonstrated the presence of alpha and kappa surface immunoglobulin (2+), PCA-1 (3+) and T10 (2+) antigens, and absence of other B cell antigens (B1, B2, B4, CALLA, I2 and HLA-DR). Representative antigen expression patterns are illustrated in FIG. 6. In addition, the following lymphocyte and macrophage associated antigens also were absent: L1, L2, L3, L4, L7, L8, 19, L11, L12, LeumM1, LeuM3 and TAC. The cells lacked expression of terminal deoxynucleotidyl transferase and EBNA. The transferrin receptor (T9 antigen) was not detected on the tumor cells, but was present on the cultured cells.

The antigen expression patterns of other B cell lines were compared to those of NCI-H929 (Table 1). The B lymphoblastoid and BL lines always expressed very high concentrations of HLA-DR, consistent expression of B1 and B4, and occasional expression of B2, CALLA and T10. In addition, some lines expressed low levels of PCA-1. EBNA was present in all LCL and some BL lines. The "plasmacytoid" lines demonstrated considerable heterogeneity. The HS Sultan and ARH 77 lines were EBNA positive and their surface antigen patterns indistinguishable from those of LCLs. U266 cells were EBNA negative and expressed PCA-1 and HLA-DR, but lacked other B antigens. RPMI 8226 lacked EBNA and HLA-DR, but expressed moderate amounts of T10 and PCA-1 and low amounts of B1 and B2.

TABLE 1

Antigen expression on B cell lines and NCI-H929 tumor and cultured cells

| Cell line type | ANTIGEN (no. positive/no. tested) | | | | | | | | |
|---|---|---|---|---|---|---|---|---|---|
| | B1 | B2 | B4 | CALLA | HLA-DR | PCA-1 | T9 | T10 | EBNA |
| B lymphoblastoid (n = 6) | 3+ (6/6) | 1+ (4/6) | 1-2+ (6/6) | 1-2+ (3/6) | 3-4+ (6/6) | 1+ (3/6) | NT | 1+ (1) | Pos. (3/3) |
| Burkitt lymphoma (n = 6) | 2-3+ (6/6) | 1-2+ (2/6) | 1-3+ (6/6) | — (0/6) | 3-4+ (6/6) | 1+ (2/6) | NT | 1-2+ (3/6) | Pos. (3/6) |
| 'Plasmacytoid' HS Sultan | 2+ | 1+ | 1+ | 1+ | 3+ | 1+ | NT | 1+ | Pos. |
| ARH 77 | 3+ | 2+ | 2+ | — | 3+ | 1+ | NT | — | Pos. |
| U266 | — | — | — | — | 3+ | 2+ | NT | NT | — |
| RPMI 8226 | 1+ | 1+ | — | — | — | 2+ | NT | 2+ | — |
| NCI-H929 tumor cells | — | — | — | — | — | 3+ | — | 2+ | NT |
| NCI-H929 cell line | — | — | — | — | — | 3+ | 2+ | 2+ | — |

EBV nuclear antigen (EBNA) was determined as previously described (7) and scored as positive or negative. Surface antigen expression was determined by flow cytometry using monoclonal antibodies as described in the text. In all positive examples >50% of the cells expressed the antigen. The degree of positive expression (1-4+) is reported as illustrated by Anderson et al. (15). All five 'plasmacytoid' cell lines expressed human forms only of the enzymes purine nucleoside phosphorylase, peptidase B, lactate dehydrogenase and glucose-6-phosphate dehydrogenase (all lines homozygous for the slow moving B form).
Pos. = positive;
— = no detectable expression;
NT = not tested Genomic blot analysis.

The state of the c-myc gene in the patient's tumor and cultured cells were examined. This analysis (FIG. 7) revealed germline and rearranged bands (12 and 14.5 kb, repectively) in both the tumor and the cell line, demonstrating that a DNA rearrangement had occurred near the c-myc gene. In the tumor cells the germline band was of greater intensity than the rearranged one, while in the cultured cells both bands were of approximately the same intensity. To determine whether the rearranged band reflected an Eco RI restriction enzyme polymorphism, the DNA samples were digested with the restriction enzymes Hind III, Sst I and Xba I. In all cases a rearranged band was seen (data not shown), ruling out a simple restriction site polymorphism. c-myc RNA was present in both the tumor and cultured cells as determined by Northern analysis (data not shown).

In summary, the results presented herein clearly demonstrate the establishment, using serum-free defined medium, of a human PC culture. The cell line has the characteristic morphology, ultrastructure and cytochemical features of PCs. It secretes very high concentrations of the same Ig class (IgAk) as did the patient's tumor cells, more than ten-fold higher than those reported for other human lines. Identical Ig gene rearrangements were detected in the tumor and cultured cells, confirming that both were derived from the same clone of malignant B cells and provide a molecular signature for the cell line.

To determine the relationship of NCI-H929 cells and other human "plasmacytoid" lines to LCL and BL lines, both of which may secrete Ig, the surface expression patterns of B cell specific and associated antigens were compared. Most normal and malignant B cells, other than PCs, express B1, B4 and Ia-like antigens (HLA-DR and I2), while B2 and CALLA have more stage restricted expression patterns. PCs and myeloma cells lack expression of these antigens, but acquire expression of a plasma cell associated antigen (PCA-1) and T10, an antigen present on various activated lymphocytes. PCs and myeloma cells lack receptors for EBV (B2 antigen) and are EBNA negative. The antigen expression patterns of NCI-H929 tumor and cultured cells were identical, except for the absence of the transferrin receptor, T9, on the former. Myeloma tumors have a low proliferative component. Expression of T9 is associated with dividing cells, including mouse myeloma cells, and it is present on the cultured cells which have a much higher proliferative fraction than the tumor cells. Both the tumor and cultured cells had antigen patterns characteristic of fully mature PCs, and could readily be distinguished from LCL and BL lines.

NCI-H929 tumor and cultured cells demonstrated an identical rearrangement of the c-myc gene. The rearranged DNA fragment was readily observable on Eco RI digests of genomic DNA, and its concentration increased relative to the germline band during culture. The use of other restriction enzyme digests excluded the possibility that the DNA rearrangement was due to a simple Eco RI restriction enzyme site polymorphism. Without being bound to any theory, it is postulated that the relative increase of the rearranged band during culture could be due to: (a) loss of contaminating stromal cells during culture; (b) selective growth of a tumor cell subpopulation having the rearrangement; or (c) selective increase in the copy number of the rearranged gene. DNA index studies excluded significant contamination of the tumor preparation with stromal cells. The tumor cells consisted predominantly of near diploid cells with a minor neartetraploid subpopulation. During culture, selective growth of the latter subpopulation occurred. The near tetraploid cells had 6 copies of chromosome 8, and 4-6 of these had an 8 q+ abnormality. In BL a reciprocal translocation occurs between the long arm of a single copy of chromosome 8 near the site of the c-myc gene (8q24) and one of the Ig loci (kapa, 2p11; mu, 14q32; lambda, 22q11). In NCI-H929 cells, no structural abnormality of chromosomes 2, 14 or 22 was apparent.

It is noted that the use of a serum free defined medium was critical for culture establishment, as the tumor cells initially failed to proliferate in serum containing media.

NCI-H929 is a highly differentiated human PC line. Antigenic and molecular studies confirm that it is derived from the patient's myeloma cells. It is an important addition to a very small, select number of human lines. It is unique in the degree of its differentiation and quantity of Ig secreted. In addition to being a potential fusion partner for human monoclonal antibody production, the culture offers a model for studying terminal B cell differentiation, Ig secretion and the relationship between human myeloma cells and the c-myc gene.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. A cultured, human plasma cell myeloma line, having a rearranged c-myc gene and having the characteristics of ATCC CRL 9068.
2. The cell line of claim 1 being cryopreserved.
3. The cell line of claim 1 capable of secreting IgAk.
4. The cell line of claim 1 capable of expressing plasma cell antigen PCA-1.
5. The cell line of claim 1 having a near tetraploid DNA content and chromosome number including six copies of chromosome 8, four to six of which have an 8 q+ abnormality.